Figure 1:
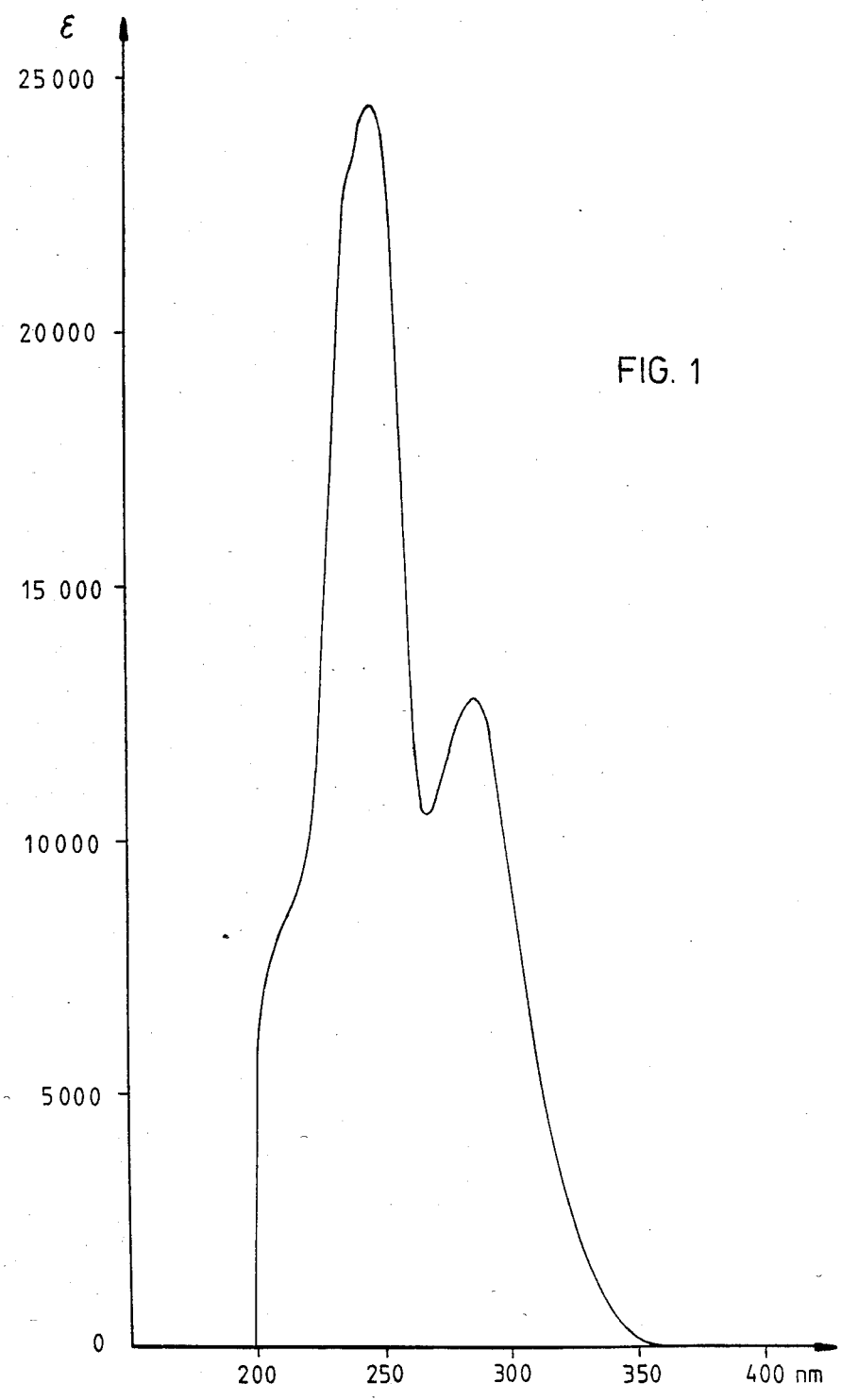

United States Patent [19]

Hagenmaier et al.

[11] Patent Number: 4,558,139
[45] Date of Patent: Dec. 10, 1985

[54] BAFILOMYCIN PESTICIDES

[75] Inventors: Hans-Paul Hagenmaier, Tuebingen; Gerhard Werner, Kusterdingen; Hannelore Drautz, Moessingen; Hartwig Holst, Pohlheim; Hans Zähner, Tuebingen; Wilhelm Brandes, Leichlingen; Paul Reinecke; Gerhard Zoebelein, both of Leverkusen; Wilhelm Stendel, Wuppertal; Peter Andrews, Wuppertal; Klaus Schaller, Wuppertal, all of Fed. Rep. of Germany

[73] Assignee: Bayer Aktiengesellschaft, Leverkusen, Fed. Rep. of Germany

[21] Appl. No.: 589,380

[22] Filed: Mar. 14, 1984

[30] Foreign Application Priority Data

Mar. 23, 1983 [DE] Fed. Rep. of Germany ....... 3310533

[51] Int. Cl.$^4$ ........................................... C07D 407/06
[52] U.S. Cl. .................................................. 549/271
[58] Field of Search ........................................ 549/271

[56] References Cited

FOREIGN PATENT DOCUMENTS 2123828 2/1984 United Kingdom ................ 549/271

Primary Examiner—Jane T. Fan

Attorney, Agent, or Firm—Sprung Horn Kramer & Woods

[57] ABSTRACT

Bafilomycins of the formula

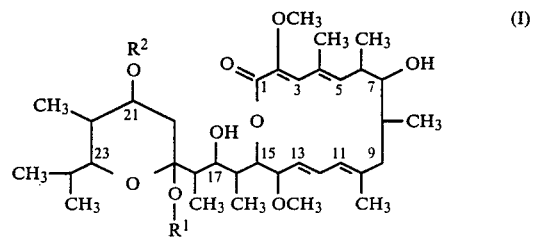

in which
$R^1$ is hydrogen or $CH_3$, and
$R^2$ is hydrogen, or the group

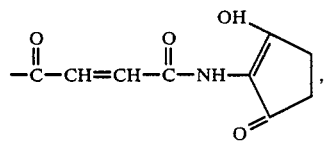

are produced by culturing certain streptomyces, e.g. Tü 1922, Tü 2437 and Tü 2599. Those wherein at least one of the OH groups is acylated are new. The compounds are pesticidally active.

16 Claims, 9 Drawing Figures

BAFILOMYCIN PESTICIDES

The present invention relates to new organic chemical compounds which, for brevity, are called bafilomycins in the following text, processes for their preparation by essentially microbiological means, and their use as agents for combating pests and parasites.

The new bafilomycins have been found, for which on the basis of the available spectroscopic and other analytical results, the following general formula I is proposed

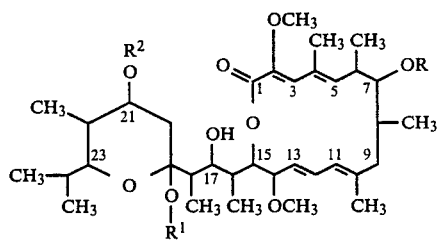

in which
R represents hydrogen or an acyl radical,
$R^1$ represents hydrogen or $CH_3$ and
$R^2$ represents hydrogen, an acyl radical or the group

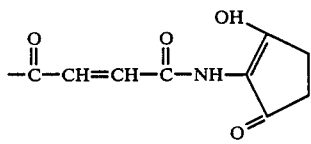

Furthermore, it has been found that the new bafilomycins can be used for combating pests and parasites of plants and warm-blooded animals. They have high efficacy against arthropods (such as insects and arachnids), fungi and worms (helminths). On the basis of these properties, the new compounds and the agents containing these compounds can be employed with particular advantage in plant protection, protection of stored products, in the area of hygiene, in the area of combating parasites, for example in animal husbandry, and in protecting materials.

The new compounds of the formula I are obtained by culturing, under aerobic conditions, microorganisms of the order Actinomycetales, preferably of the family Streptomycetaceae, in particular of the genus Streptomyces, in a customary manner in a nutrient medium which contains sources of assimilable carbon and nitrogen as well as mineral salts, isolating and optionally acylating the desired compounds by customary methods.

Knowing the properties of the new compounds according to the invention, it is possible, using customary chromatographic, spectroscopic and/or microbiological (for example the zone of inhibition test) methods, to seek out, readily and rapidly in routine procedures, those strains of microorganisms which are suitable to produce bafilomycins according to the invention.

Strains of *Streptomyces griseus* are preferably employed for the microbiological preparation of the compounds according to the invention. Very particularly preferred for this purpose are the strains of *Streptomyces griseus* Tü 1922, Tü 2437 and Tü 2599 and the variants and mutants of these strains which exhibit the characteristics essential for carrying out the present invention.

The strains Tü 1922, Tü 2437 and Tü 2599 have been deposited at the Deutschen Sammlung von Mikroorganismen (DSM), [The German Collection of Microorganisms], Grisebachstrasse 8, 3400 Göttingen, Federal Republic of Germany:

| Trivial name of strain | Deposition File Number | Date |
|---|---|---|
| Tu 1922 | DSM 2608 | March 7, 1983 |
| Tu 2437 | DSM 2609 | March 7, 1983 |
| Tu 2599 | DSM 2610 | March 7, 1983 |

Description of the strain Tü 1922:

The strain Tü 1922 was isolated from a sample of soil from Kaziranga (Assam), India, and exhibits the following characteristics:
Surface of spores: smooth
Spore size: $0.8-1.1 \times 0.37-0.5\mu$
Color of the aerial mycelium: greenish-blue-gray (griseus)
Spore chains: straight and slightly wavy in clusters, no spirals.
Melanin formation: none There is no doubt that the strain is of the species *Streptomyces griseus*.

Description of the strains TÜ 2437 and Tü 2599:
The strain Tü 2437 originates from a sample of soil from Thailand and the strain Tü 2599 was isolated from a sample of soil from Peru.

Identification was carried out by the method of:
R. Hütter: Systematik der Streptomyceten [Systematics of the Streptomycetes], Karger Verlag, Basel 1967
T. G. Pridham and H. D. Tresner: Streptomycetaceae, in Bergey's Manual of Determinative Bacteriology, 8th Edition, 1974, Williams & Wilkins Comp., Baltimore.
Description of the strains:
Surface of the spores: smooth
Spore sizes: $0.8-1.0 \times 0.5-0.7\mu$
Color of the aerial mycelium: initially white, later greenish-gray (griseus).
Morphology of spore chains: spore chains straight or slightly wavy, no spirals, no whorls.
Melanin formation: none
Utilization of various C sources:

| | |
|---|---|
| D-glucose | + |
| l-arabinose | − |
| sucrose | ± (−) |
| D-xylose | + |
| m-inositol | − |
| D-mannitol | + |
| D-fructose | + |
| rhamnose | − |
| raffinose | ± |
| cellulose | − |
| galactose | + |

(+ denotes utilization and
− denotes no utilization).

The two strains agree in all characteristics and are regarded as typical representatives of the species *Streptomyces griseus*.

The compounds of the formula I in which R and/or $R^2$ represent an acyl radical can be obtained by acylation of the microbiologically produced compounds in which R and/or $R^2$ denote hydrogen.

The acyl radicals R and $R^2$ preferably represent alkyl-CO- radicals in which alkyl is straight-chain or branched and preferably contains 1 to 6, especially 1 to 4, carbon atoms, methyl, ethyl, n- and i-propyl, and n-, sec-, i- and t-butyl being mentioned as examples. The acyl radicals R and $R^2$ very particularly preferably represent the acetyl group ($CH_3$—CO—).

The following bafilomycins should be mentioned as preferred compounds of the formula I:

| Trivial name: | Meaning of the radical in formula I: | | |
|---|---|---|---|
| | R | $R^1$ | $R^2$ |
| Bafilomycin $A_1$ | H | H | H |
| Bafilomycin $A_2$ | H | $CH_3$ | H |
| Bafilomycin $B_1$ | H | H | 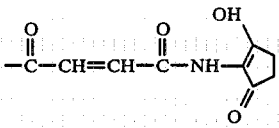 |
| Bafilomycin $B_2$ | H | $CH_3$ | " |
| Bafilomycin $D_1$ | H | H | —$COCH_3$ |
| Bafilomycin $D_1$) | —$COCH_3$ | H | —$COCH_3$ |
| Bafilomycin $D_2$ | H | $CH_3$ | —$COCH_3$ |
| Bafilomycin $D_2$) | —$COCH_3$ | $CH_3$ | —$COCH_3$ |

Among the bafilomycins mentioned, bafilomycins $A_1$, $A_2$, $B_1$ and $B_2$ should be picked out as being particularly preferred compounds according to the invention. Bafilomycins $A_1$ and $A_2$ are very particularly preferred.

As already explained above, bafilomycins $D_1$ and $D_1$) can be obtained by customary acetylation methods (for example with acetyl chloride or acetic anhydride) from bafilomycin $A_1$.

Figure 2:
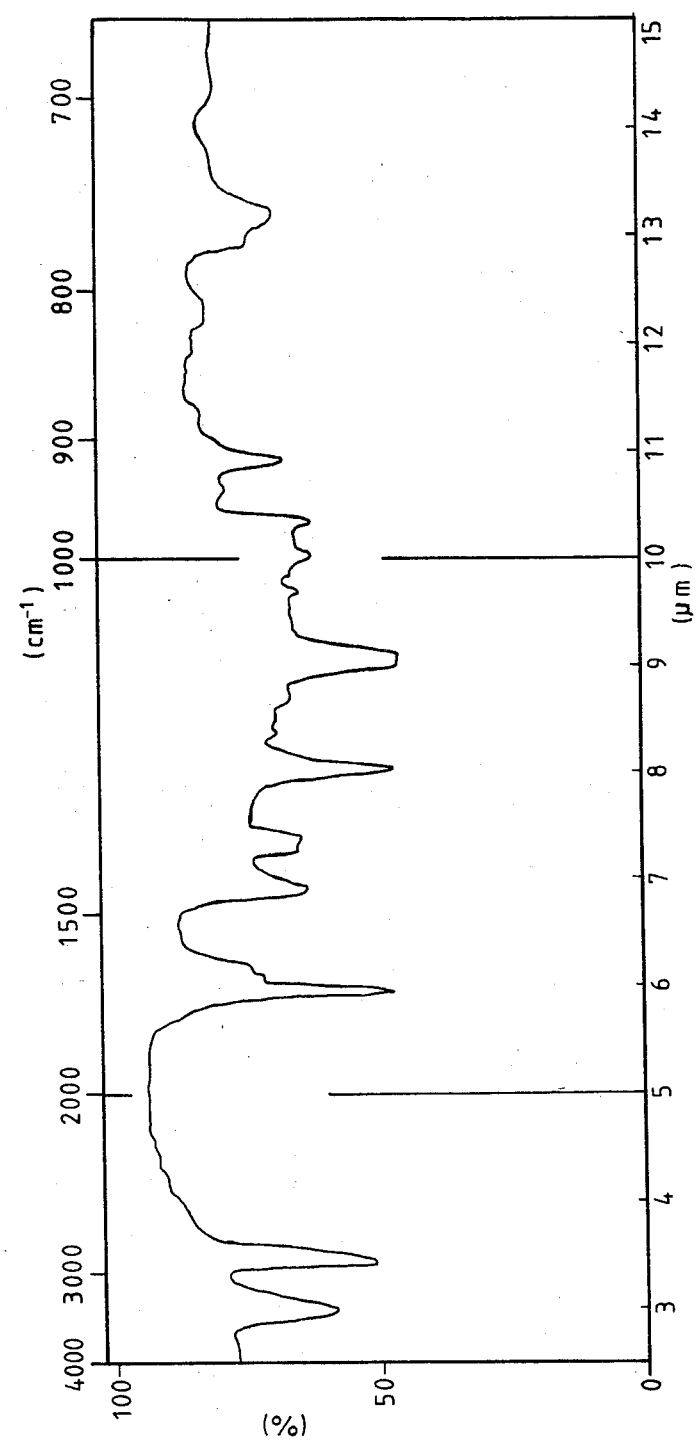
Figure 3:
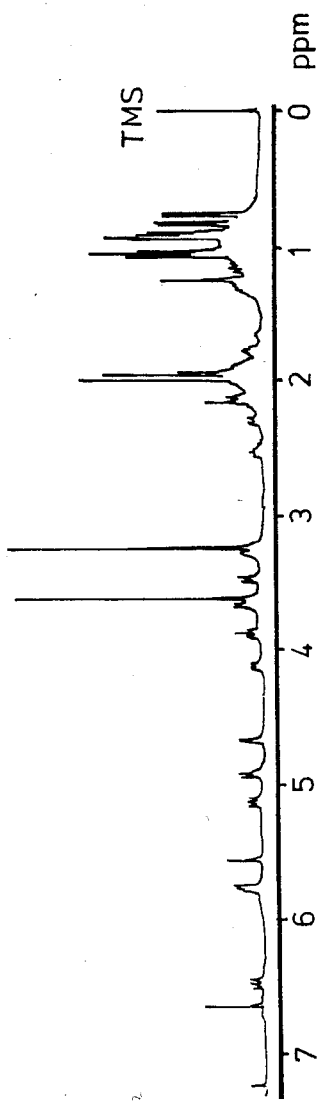

The structures of the new compounds according to the invention have been determined on the basis of comprehensive analytical, especially spectroscopic, investigations. However, since errors of interpretation of the analytical findings cannot always be completely excluded for substances of complicated structure, the preferred bafilomycins are also to be charaterized by some physicochemical data:

1. Bafilomycin $A_1$:
Appearance: colorless amorphous powder.
Melting point: 98°–106° C. (decomposition).
Solubility:
 readily soluble in methanol,
 readily soluble in chloroform,
 sparingly soluble in water.
Thin-layer chromatogram (silica gel):
 $CHCl_3$:$CH_2OH$ (9:1 parts by volume),
 Rf: 0.51.
Ethyl methyl ketone: $CHCl_3$ (1:1 parts by volume)
 Rf: 0.42.
Ethyl methyl ketone: Rf: 0.86.
Acetone: Rf: 0.91.
Molecular weight: 622.
Molecular formula (elemental analysis): $C_{35}H_{58}O_9$.
Spectra:
 UV: FIG. 1,
 IR: FIG. 2,
 NMR: FIG. 3.
2. Bafilomycin $A_2$:
Appearance: colorless amorphous powder.

Figure 4:
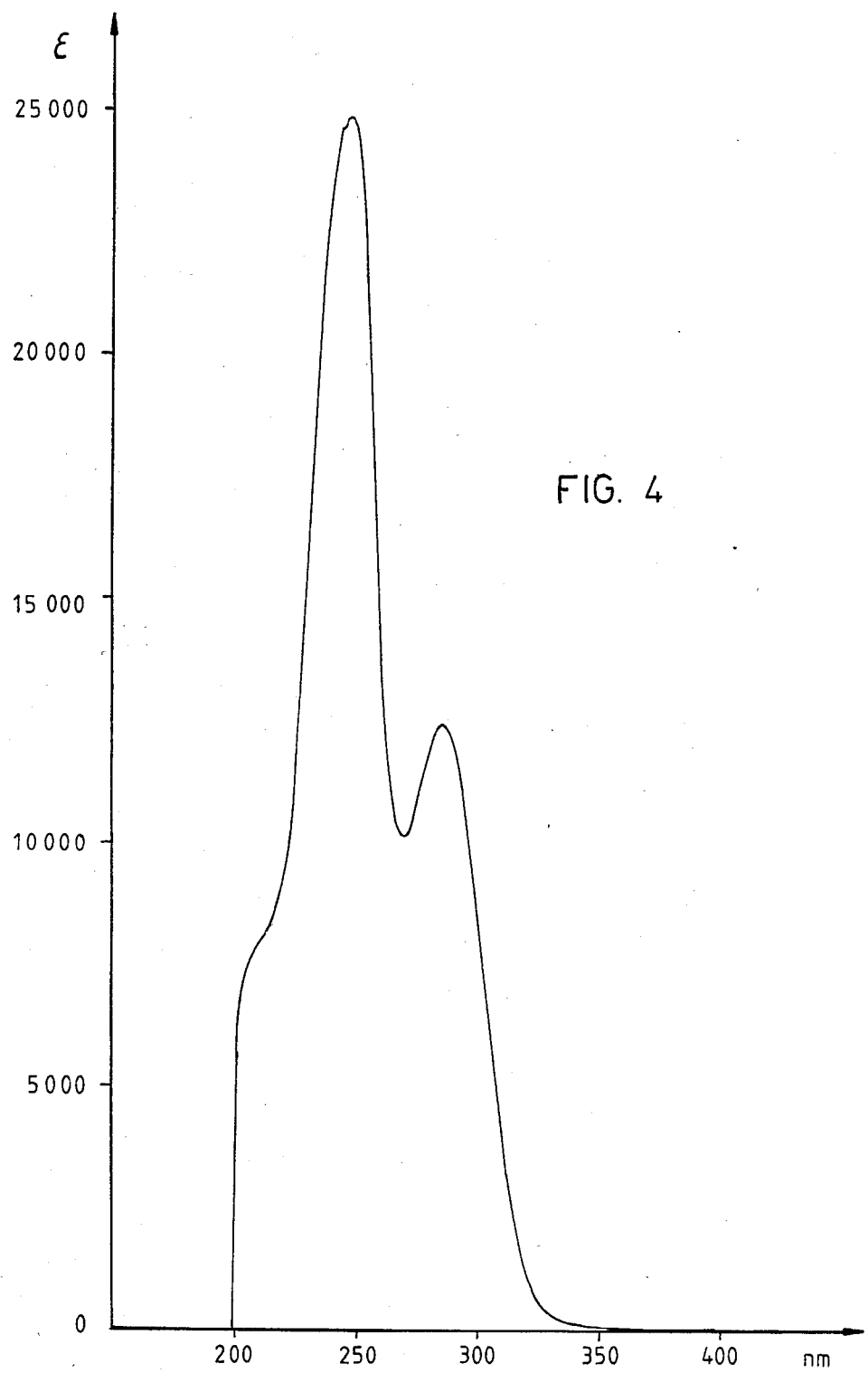
Figure 5:
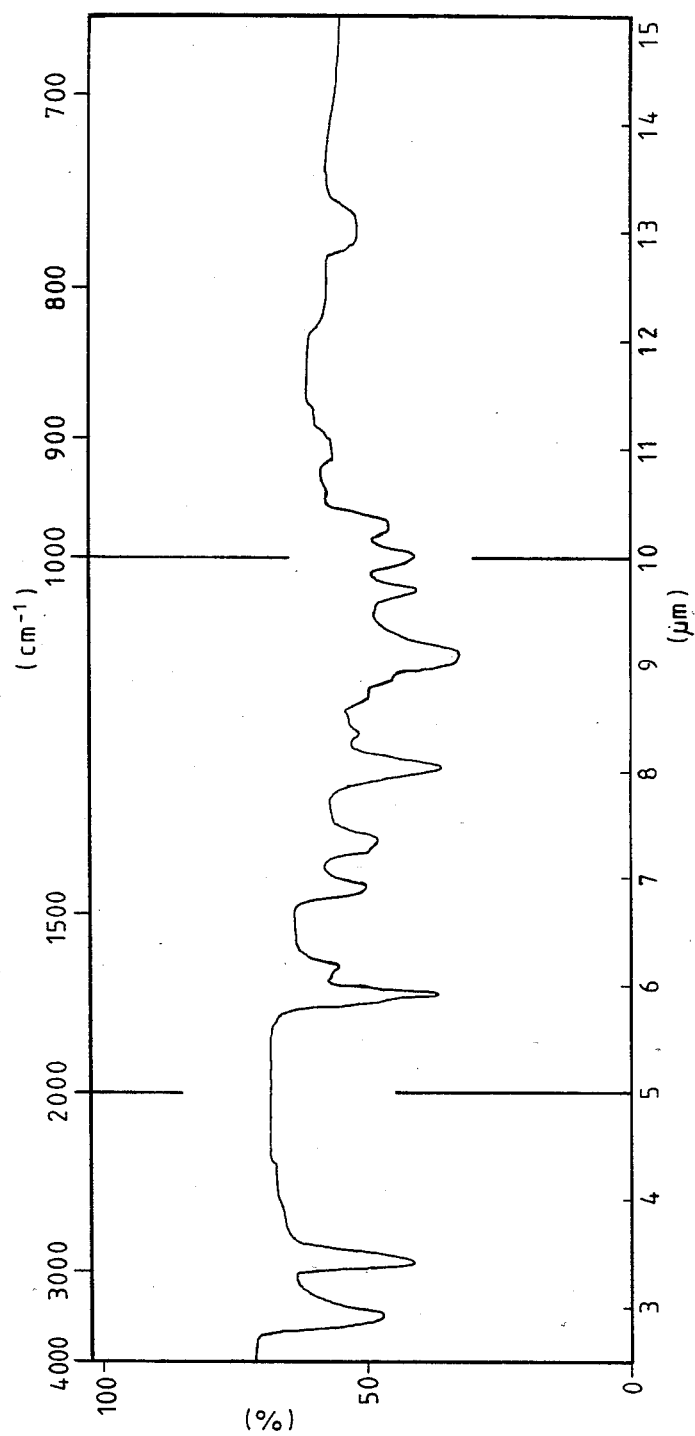
Figure 6:
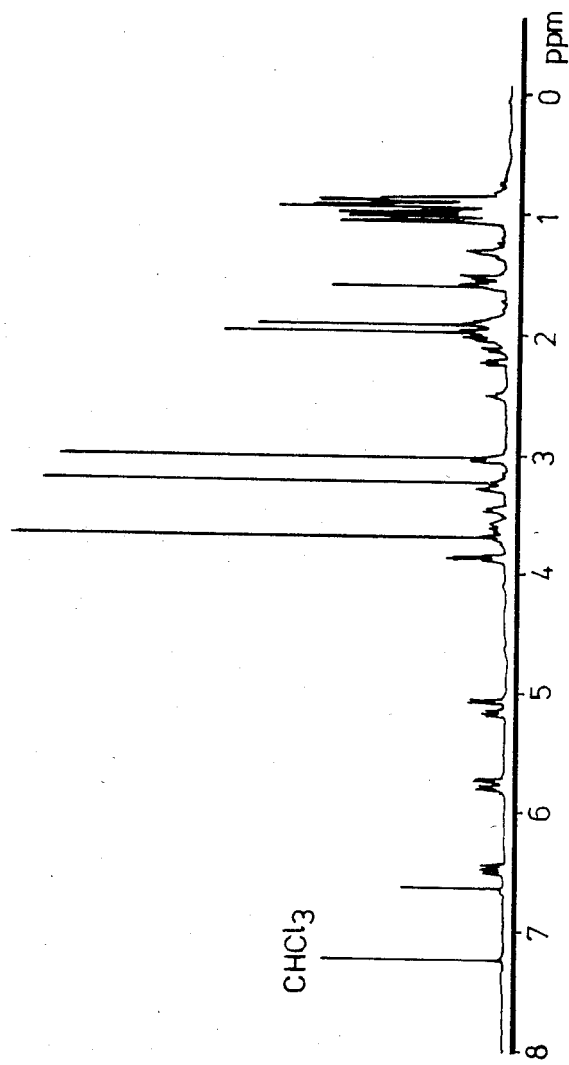
Figure 7:
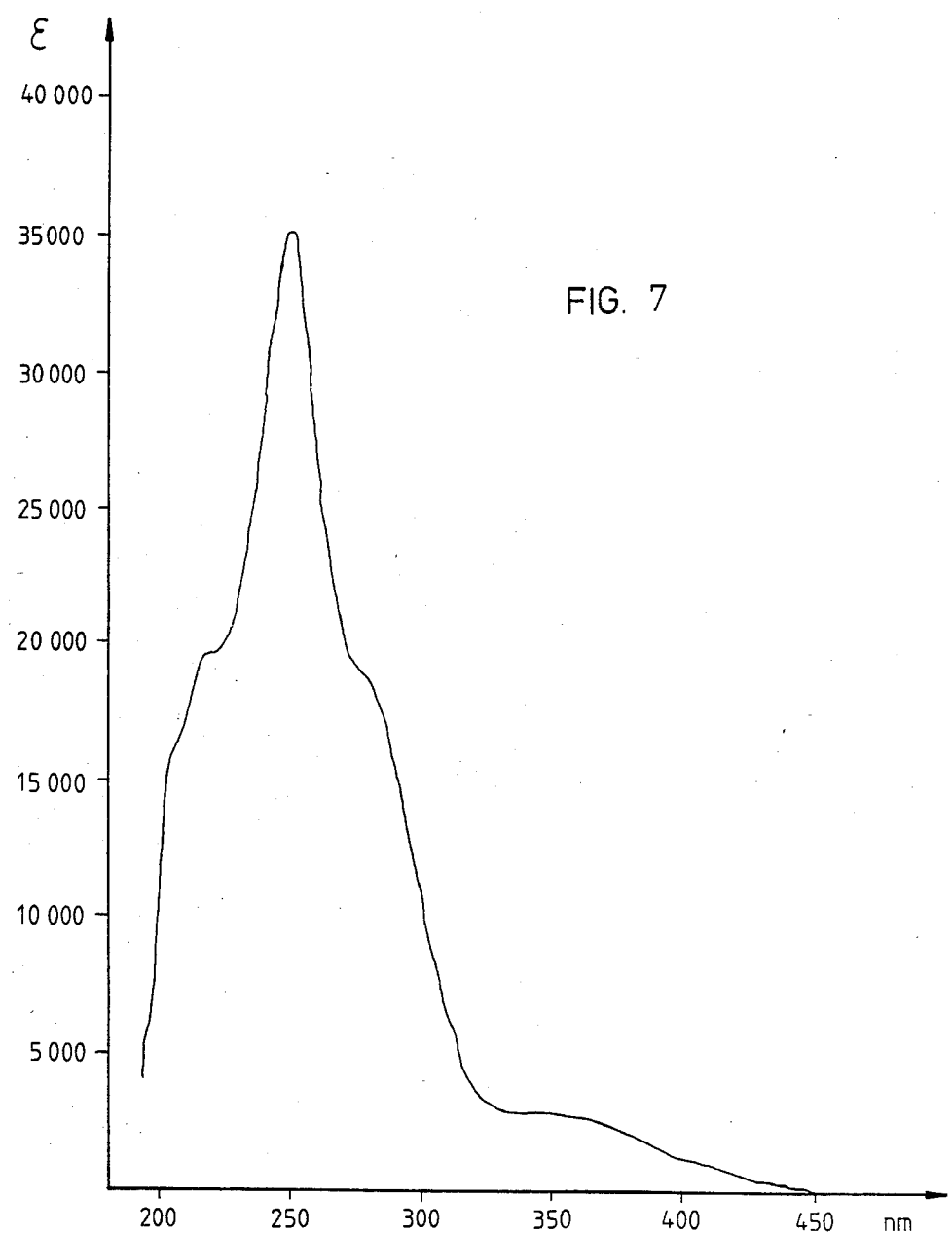
Figure 8:
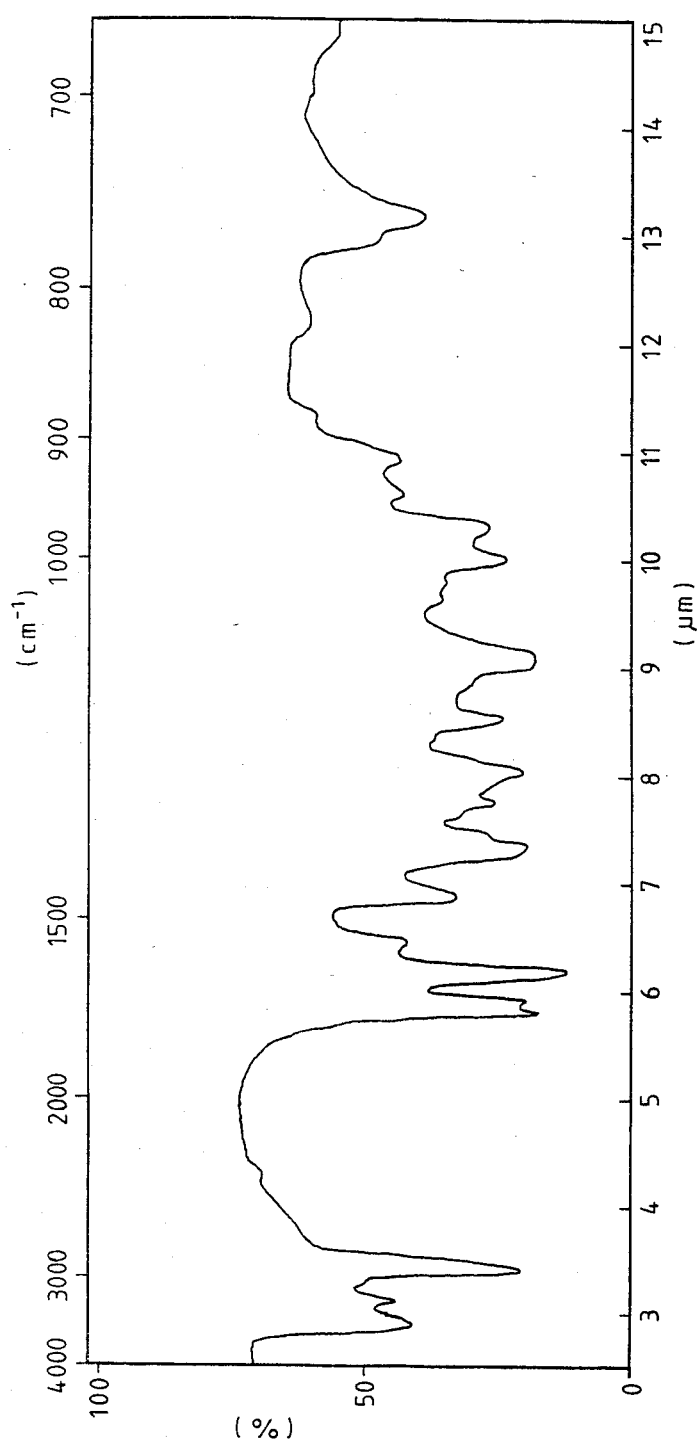
Figure 9:
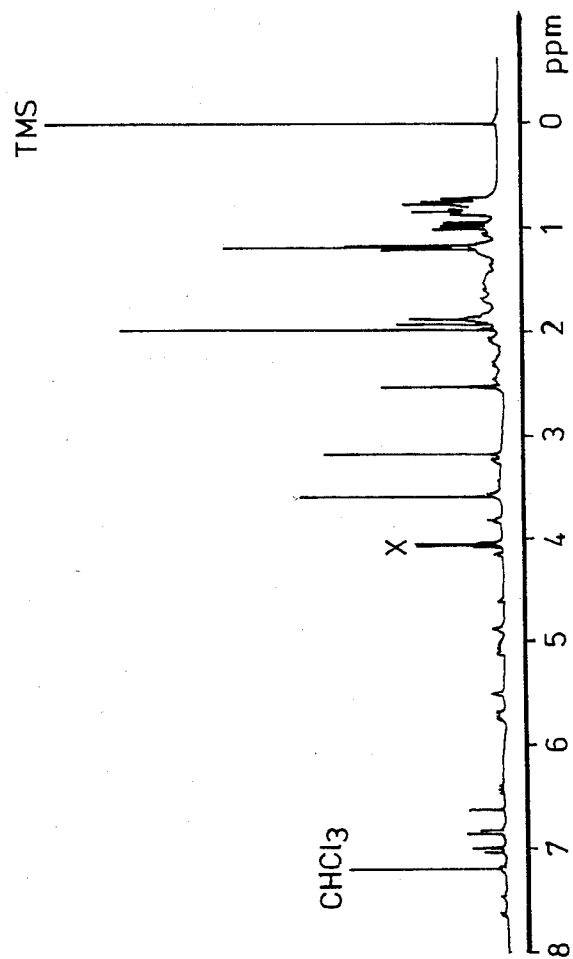

Melting point: 116°–119° C. (decomposition).
Solubility:
 readily soluble in methanol,
 readily soluble in chloroform,
 sparingly soluble in water.
Thin-layer chromatogram:
 $CHCl_3$:$CH_3OH$ (9:1 parts by volume),
 Rf: 0.52.
Ethylene methyl ketone: $CHCl_3$ (1:1 parts by volume)
 Rf: 0.42.
Acetone: Rf: 0.91.
Molecular weight: 636.
Molecular formula (elemental analysis): $C_{36}H_{60}O_9$.
Spectra:
 UV: FIG. 4,
 IR: FIG. 5,
 NMR: FIG. 6.
3. Bafilomycin $B_1$:
Appearance: amorphous powder with an intense yellow color.
Melting point: 89°–96° C. (decomposition).
Solubility:
 readily soluble in methanol,
 readily soluble in chloroform,
 readily soluble in pyridine,
 soluble in ethyl acetate,
 sparingly soluble in water.
Thin-layer chromatogram (silica gel):
 $CHCl_3$:$CH_3OH$ (9:1 parts by volume),
 Rf: 0.43.
Ethyl methyl ketone: $CHCl_3$ (1:1 parts by volume)
 Rf: 0.37.
Ethyl methyl ketone: Rf: 0.78.
Acetone: Rf: 0.76.
Molecular weight: 815.
Molecular formula (elemental analysis): $C_{44}H_{65}O_{13}N$.
Spectra:
 UV: FIG. 7,
 IR: FIG. 8,
 NMR: FIG. 9.

The acylation according to the invention of the bafilomycins (R and $R^2$=hydrogen) can be carried out in a customary manner, the customary acylating agents, such as acid halides or anhydrides being used. It can be advantageous to add bases (preferably organic bases, such as pyridine) in this reaction. The acylating agent is preferably employed in excess, and the reaction is carried out under mild conditions, for example at room temperature (about 17°–25° C.). The product of acylation can, if desired, be isolated and purified by chromatographic methods.

The new bafilomycins are produced according to the invention by the fermentation of suitable strains of microorganisms, such as Tü 1922, Tü 2437 and Tü 2599 or their mutants or variants.

The fermentation process according to the invention can be carried out using solid, semisolid or liquid nutrient media. Aqueous liquid nutrient media are preferably used.

The nutrient media are inoculated by generally customary methods, for example via slant tubes or flask cultures.

Culturing takes place under aerobic conditions and can be carried out according to the generally customary methods, such as using shaking cultures, for example in shaking flasks, using cultures agitated by air or using submersed cultures. Culturing preferably takes place in an aerobic submersed process in aerated fermenters, for example in customary submersed fermentation tanks. It is possible to carry out the culturing continuously or discontinuously. Discontinuous operation is preferred.

The culturing can be carried out in all nutrient media which are known to be used for culturing microorganisms of the order Actinomycetales. The nutrient medium must contain one or more sources of assimilable carbon and nitrogen as well as mineral salts, it being possible for these products to be present in the form of defined individual constituents or in the form of complex mixtures as are represented by, in particular, biological products of various origins. All customary sources of carbon are suitable as sources of carbon. Examples which may be mentioned are carbohydrates, especially polysaccharides, such as starch or dextrins, disaccharides, such as maltose or sucrose, monosaccharides, such as glucose or xylose, sugar alcohols, such as mannitol or glycerol, and naturally occurring mixtures, such as malt extract, molasses or whey powder. All customary organic and inorganic sources of nitrogen are suitable as sources of nitrogen. Examples which may be listed are proteins, protein hydrolyzates, amino acids, such as glutamic acid, aspartic acid, arginine, lysine, ornithine or serine, nucleoside bases, such as cytosine or uracil, as well as soy bean meal, cottenseed meal, lentil meal, pease meal, soluble and insoluble vegetable proteins, cornsteep liquor, yeast extract, peptone and meat extract, as well as ammonium salts and nitrates, for example $NH_4Cl$, $(NH_4)_2SO_4$, $NaNO_3$ and $KNO_3$. The mineral salts which should be contained in the nutrient medium provide the following ions, for example: $Mg^{++}$, $Na^+$, $K^+$, $Ca^{++}$, $NH_4^+$, $Cl^-$, $SO_4^{--}$, $PO_4^{---}$ and $NO_3^-$ and ions of the customary trace elements, such as Cu, Fe, Mn, Mo, Zn, Co and Ni. If the sources of carbon or nitrogen or the water which is used do not contain adequate amounts of these salts or trace elements, it is advantageous to supplement the nutrient medium appropriately. The composition of the nutrient medium can be varied within wide limits. The type and the composition of the nutrient media will generally depend on the components which are available particularly favorably in each case. In general, the nutrient solutions preferably contain about 0.5 to 8%, in particular 0.6 to 6%, of sources of carbon, preferably about 0.5 to 4%, in particular 0.5 to 2%, of sources of nitrogen and preferably about 0.001 to 0.5%, in particular 0.003 to 0.3%, of mineral salts.

In carrying out the process according to the invention, in can be favorable to use only relatively low concentrations of the soluble components of the nutrient solution at the start of culturing, and then to feed in these components in fractions in the form of a sterile and relatively concentrated solution which is relatively frequently added during the first 3 days of culturing.

The pH of the growing cultures should preferably be maintained between about 5 and about 10, in particular between 6.5 and 9.5. Too great a decrease in pH into the acid range can be prevented by adding an organic or inorganic base, preferably $CaCO_3$. As is customary in the technology of fermentation, automatic control of the pH can also be carried out, in which sterile organic or inorganic acids, for example $H_2SO_4$, or sterile solutions of alkali, for example NaOH, are injected into the culture solution at intervals.

It is advantageous to ensure that the microorganisms are brought into adequate contact with oxygen and with the nutrients. This can take place by the generally customary methods, such as shaking and stirring.

The temperature of culturing can be between about 15° and about 40° C., preferably between 20° and 35° C., and particularly preferably at about 28° C. The duration of culturing can be varied widely, the composition of the nutrient medium and the temperature of culturing, for example, being of importance. The optimum conditions in each case can be readily determined by those skilled the art of microbiology.

It has emerged that the amount of the compound according to the invention which accumulates in the culture broth generally reaches its maximum about 1 to 10, preferably about 3 to 5 days, after starting culturing. The desired final product of fermentation can be determined using thin-layer chromatographic and high-pressure liquid chromatographic investigations or in the plate diffusion test using a suitable fungus as the test strain.

As is general in microbiological processes, foreign infection of the culture media should be prevented. The customary measures are undertaken for this purpose, such as sterilization of the nutrient media, of the culture vessels and of the air necessary for aeration. It is possible to use, for example, steam or dry sterilization for sterilizing the equipment, it being possible for the temperatures to be, preferably 100° to 140° C., in particular 120° to 130° C.

If foam is produced to an undesirable extent during culturing, it is possible to add the customary chemical foam suppressants, for example liquid fats and oils, oil/water emulsions, paraffins, higher alcohols, such as octodecanol, silicone oils, polyoxyethylene or polyoxypropylene compounds (for example in amounts of up to about 1%). Foam can also be suppressed or abolished using the customary mechanical equipment (which utilize, for example, centrifugal forces).

The compounds according to the invention can be isolated from the culture medium using generally customary physicochemical methods. For example, isolation can take place using the customary extraction processes, precipitation processes and/or chromatographic processes. The isolated substances can also be finally purified using the methods mentioned. However, final purification is unnecessary in many cases, since any impurities which are present in small amounts do not adversely affect the efficacy of the compounds. Care has to be taken in all isolation and purification operations that the pH is not in the acid range for a prolonged period. pH values between 7 and 10 are preferably maintained. It is possible to use inorganic and and organic bases to lower the pH, such as alkali metal bases, for example NaOH or KOH, or organic amines, such as triethylamine.

In order, in the abovementioned isolation and purification methods, to discover the fractions in which the compounds according to the invention are present in the highest concentration or purity, it is possible to employ the customary physicochemical methods, for example measurement of a characteristic band in the spectrum or the $R_f$ values, determination of the antimicrobial activity etc. These methods can also be used in order to discover suitable microorganisms in routine procedures.

The isolation and purification of the compounds according to the invention can be undertaken, for example in the case where a liquid aqueous nutrient medium is used, as follows: after its accumulation in the culture supernatant, the filtrate from the culture and the mycelium are separated by customary methods (for example centrifugation).

The compounds according to the invention can be isolated from the filtrate from the culture and, where appropriate, purified using customary extraction processes, precipitation processes and/or chromatographic processes. The chromatography can be carried out in the form of column chromatography. High-pressure liquid chromatography (HPLC) can also be employed with good results. The customary inorganic or organic adsorption agents can be employed as the adsorption agent, such as, for example, aluminum oxide, silica gel, magnesium silicate, active charcoal, cellulose, cellulose derivatives, artificial resins, such as polyamides, for example acetylated polyamide or dextran gels. A wide variety of solvents or solvent mixtures can be used as the mobile phase, in which the compounds according to the invention are soluble. Ethyl acetate, chloroform and methanol or their mixtures (for example mixtures of chloroform and methanol or of ethyl acetate and chloroform) are preferably employed. The bafilomycins should only be left in contact with methanol for as long as is necessary.

Chromatographic processes are preferably used for isolating the compounds according to the invention, for example non-specific adsorption on sorbents, such as silica gel or, on the other hand, gel diffusion chromatography. These are methods known for the purification of natural substances which are poorly soluble in water.

The compounds according to the invention can be obtained from solutions by the customary methods, for example by evaporating the solvent, freeze-drying, etc.

In a preferred embodiment of the invention, the fermentation material (culture broth and mycelium) obtained on aerobic culture of the strains at about 27° C. is extracted with a polar solvent, such as ethyl acetate, several times, preferably 3 times. The combined extracts are dried with sodium sulphate and the solvent is removed by distillation (preferably under high vacuum at about 0° C.).

The crude bafilomycin product is then subjected to preparative fractional column chromatography. Silica gel is preferred as the adsorption agent for this purpose. Preferred eluants are mixtures of polar solvents, in particular of chloroform and methanol, a ratio of about 1:1 (parts by volume) providing particularly favorable results. The fractions can readily be assigned on the basis of thin-layer chromatographic investigations. The crude bafilomycins $A_1/A_2$ and $B_1/B_2$ are obtained in this manner. The crude bafilomycins are further purified by column chromatography (preferably on silica gel with the preferred eluants chloroform/methanol and, in the case of $B_1/B_2$, also with chloroform/ethyl acetate. Final purification of the products obtained in this manner (which are already very pure) is advantageously carried out by high-pressure liquid chromatography (HPLC) using customary equipment, the preferred packing being customary "reversed phase" materials, such as silica gel modified with paraffin, and the preferred eluants are methanol/water mixtures.

The active compounds are well tolerated by plants, have a favorable level of toxicity to warm-blooded animals, and are suitable for combating animal pests, especially insects, arachnids and nematodes, which are encountered in agriculture, in forestry, in the protection of stored products and of materials, and in the hygiene field. They are active against normally sensitive and resistant species and against all or some stages of development. The abovementioned pests include:

From the order of isopoda, for example Oniscus asellus, Armadillidium vulgare, Porcellio scaber.

From the order of diplopoda, for example Blaniulus guttulatus.

From the order of chilopoda, for example Geophilus carpophagus, Scutigera spec.

From the order of symphyla, for example Scutigerella immaculata.

From the order of thysanura, for example Lepisma saccharina.

From the order of collembola, for example Onychiurus armatus.

From the order of orthoptera, for example Blatta orientalis, Periplaneta americana, Leucophaea maderae, Blattella germanica, Acheta domesticus, Gryllotalpa spp., Locusta migratoria migratorioides, Melanoplus differentialis, Schistocerca gregaria.

From the order of dermaptera, for example Forficula auricularia.

From the order of isoptera, for example Reticulitermes spp..

From the order of anoplura, for example Phylloxera vastatrix, Pemphigus spp., Pediculus humanus corporis, Haematopinus spp., Linognathus spp.

From the order of mallophaga, for example Trichodectes spp., Damalinea spp.

From the order of thysanoptera, for example Hercinothrips femoralis, Thrips tabaci.

From the order of heteroptera, for example Eurygaster spp., Dysdercus intermedius, Piesma quadrata, Cimex lectularius, Rhodnium prolixus, Triatoma spp.

From the order of homoptera, for example Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma Lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata Lugens, Aonidiella aurantii, Aspidiotus hederae, Pseudococcus spp. Pyslla spp.

From the order of Lepidoptera, for example Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia Litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Chroistoneura fumiferana, Clysia ambiguella, Homona magnanima, Tortrix viridana.

From the order of coleoptera, for example Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., *Niptus hololeucus, Gibbium psylloides*, Tribolium spp., *Tenebrio molitor*, Agriotes spp., Conoderus spp., *Melolontha melolontha, Amphimallon solstitialis, Costelytra zealandica.*

From the order of hymenoptera, for example Diprion spp., Hoplocampa spp., Lasius spp., *Monomorium pharaonis*, Vespa spp.

From the order of diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hypopobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae, Tipula paludosa.*

From the order of siphonaptera, for example *Xenopsylla cheopis*, Ceratophyllus spp..

From the order of arachnida, for example *Scorpia maurus, Latrodectus mactans.*

From the order of acarina, for example *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp..

The phytoparasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp., Trichodorus spp..

The active compounds according to the invention exhibit strong microbicidal activity and can be employed in practice for combating undesired microorganisms. The active compounds are suitable for use as plant-protection agents.

Fungicidal agents are employed in plant protection for combating plasmodiophoromycetes, oomycetes, chytridiomycetes, zygomycetes, ascomycetes, basidiomycetes and deuteromycetes.

Bactericidal agents are employed in plant protection for combating pseudomonadaceae, rhizobiaceae, enterobacteriaceae, corynebacteriaceae and streptomycetaceae.

The active compounds are well tolerated by plants in the concentrations necessary for combating plant diseases, and this permits treatment of parts of the plant above the ground, of plant and seed materials, and of the soil.

The active compounds according to the invention are also suitable for combating ectoparasites and endoparasites in warm-blooded animals, for example in the areas of animal husbandry and cattle breeding, it being possible to achieve improved results, for example higher milk yields, higher weights, longer lives etc. by combating the pests.

The use of the active compounds according to the invention in these areas takes place in a known manner, such as by oral administration in the form of, for example, tablets, capsules, drinks and granules, by dermal application, for example in the form of dipping, spraying, pouring on and spotting on, and dusting, and by parenteral administration, for example in the form of an injection.

Moreover, these areas also comprise, for example, ticks and those arthropods, part of whose development takes place in the animal. Furthermore, the compounds according to the invention are also suitable for combating worms, especially those of the class of nematodes, which are parasites of warm-blooded animals. In addition, the compounds according to the invention can be used for combating dermal fungal infections in warm-blooded animals.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dipersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aeerosol propellants, such as halogenated hydrocarbons as well as butane, propane, nitrogen and carbon dioxide; as solid carriers there are suitable: for example ground natural minerals, such as kaolines, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphate waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian blue, and organic dyestuffs, such as alizarin dyestuffs, azo dyestuffs and metal-phthalocyanine dyestuffs, and trace nutrients, such as salts of iron, manganese, boron, copper, cobalt, molybdenum and zinc.

The formulations generally contain between 0.1 and 95 percent by weight of active compound, preferably between 0.5 and 90%.

The active compounds according to the invention can be present in their commercially available formulations and in the use forms prepared from these formulations as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, and substances produced by microorganisms.

The active compounds according to the invention can furthermore be present in their commercially available formulations and in the use forms prepared from these formulations as a mixture with synergistic agents. Synergistic agents are compounds which increase the action of the active compounds without it being necessary for the added synergistic agent to be itself active.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The new bafilomycins cannot only be used as active ingredients but also be used as valuable intermediates for the preparation of new active ingredients (particularly from bafilomycins $A_1$ and $A_2$).

The preparation of the compounds according to the invention is to be illustrated by means of the examples which follow. Unless otherwise specified, all percentage data refer to percent by weight. Acetic ester denotes ethyl acetate.

I. Examples of fermentation of the strains Tü 1922, Tü 2437 and Tü 2599

1. Fermentation of the strain Tü 1922

The strain Tü 1922 is kept in a slant agar tube at about 4° C. in a cool room. The HA agar used for this purpose contains 4 g of yeast extract, 10 g of malt, 4 g of dextrose and 15 g of agar (remainder: water) per liter, and has a pH of 7.3. Solutions of spores of the strain Tü 1922 are stored at −20° C.

For the fermentation, a nutrient solution (NL 111) is employed which, in addition to tap water, contains 2% of meat meal, 2% of malt extract and 1% of lime, and has a pH of 7.2.

(a) Procedure on the flask scale 500 ml conical flasks having a septum on the side and containing 100 ml of nutrient solution (NL 111) are inoculated from a slant agar culture and incubated on a rotating shaking machine at 120 rpm (rotations per minute) and 27° C. for 4 days. A 48 hour-old culture serves as the preculture for the 10 liter fermenter.

(b) Procedure in a 10 liter fermenter

The fermentation is carried out in a 10 liter fermenter (model MF-14 New Brunswick, Scientific Co., New Brunswick, USA), which contains 9 liter of nutrient solution (NL 111). Sterilization is carried out at 134° C. for 30 minutes. 4 liters of air per minute are passed into the culture liquid (2 liters of air per minute are used as a prefermenter for the 100 liter fermenter) at an incubation temperature of 27° C. and the stirrer at 250 rpm. Development of foam is suppressed by repeated addition of a few drops of ethanolic polyol solution. The amount of material inoculated is 5% of one of the cultures described under (a).

Harvesting is carried out after about 70 hours.

(c) Procedure in a 100 liter fermenter

The material used for inoculation is the contents of a 10 liter fermenter (compare b) after fermentation for 48 hours. The 100 liter fermenter contains a total of 90 liters of material (including material for inoculation). The nutrient solution used is the nutrient medium NL 111 (compare above). The incubation time up to maximum production of bafilomycin is about 70 hours at 200 rpm of the blade stirrer, 50 liters of air being passed in per minute and the temperature being maintained at about 27° C.

2. Fermentation of the strain Tü 2437

The strain Tü 2437 is stored as described above for strain Tü 1922.

The nutrient solution used for the fermentation is a preparation comprising tap water, 2% of soy meal and 2% of lactose and having a pH of 7.5.

(a) Procedure on the flask scale

The procedure is as described for strain Tü 1922, but the soy meal/lactose nutrient solution is used.

(b) Procedure in a 100 lit fermenter

The procedure is as described for strain Tü 1922. However, the soy meal/lactose nutrient solution is employed. 360 liters of air are passed in each hour while stirring with a blade stirrer (240 rpm), and the fermentation is carried out at 27° C. for 24.5 hours.

(c) Procedure in a 100 liter fermenter

The batch obtained according to (b) is introduced as the material for inoculation into the 100 liter fermenter. The volume is made up to 90 liters using the above soy meal/lactose nutrient solution. 3,400 liters of air are passed in to the mixture per hour, stirring with a blade stirrer (200 rpm), and the fermentation is carried out, with the addition of about 30 ml of ethanolic polyol solution (as a defoamer), at 27° C. for 71.5 hours.

3. Fermentation of the strain Tü 2599

The strain Tü 2599 is stored as described above for strain Tü 1922.

The procedure for fermentation on the flask scale and in the 10 and 100 liter fermenters is exactly as described for the fermentation of the strain Tü 2437.

II. Examples for the working up of the culture broths obtained according to I

1. Preparation of the crude bafilomycin extract solution

The material from the fermentation is adjusted to a pH of 6 (strains Tü 2437 and Tü 2599) by the addition of acetic acid, or to a pH of 10 (strain Tü 1922) by the addition of 10% aqueous NaOH. The mycelium formed is then separated out using a filter press. The mycelium can be immediately discarded or, preferably, extracted beforehand with the object of increasing the yield of bafilomycin. The extracting agent used for this purpose is a mixture of methanol and acetone (1:1 parts by volume). A total of about 2,000 ml of the mixture of solvents is employed for 1 kg of mycelium. The mycelium is extracted 3 times with the mixture of solvents and then discarded. The mixture of solvents is removed from the solution by distillation under high vacuum at 0° C. The residue is taken up in acetic ester (about 50 ml of acetic ester per 1 g of residue) and filtered to remove solid components.

The culture broth which has been freed of mycelium is extracted 3 times with a total of about 20 parts by volume of acetic acid ester for each 100 parts by volume of culture broth. The acetic ester extracts from the culture broth and mycelium are combined and dried with sodium sulphate. The solution is concentrated by distillation under high vacuum at 0° C. to about 1/10 of the original volume. Thus, in the case of fermentation in a 100 liter fermenter, about 2 liters of acetic ester solution are obtained (crude extract solution).

2. Rough purification of the crude bafilomycin extract 2 liters of the crude extract solution obtained according to 1 are extracted by shaking with a little (500 ml) of water at pH 7.0. The water extract is back-extracted twice with acetic ester. All the acetic ester phases are combined, dried with sodium sulphate, filtered and the solvent is removed down to 500 ml by distillation under high vacuum at 0° C. After 24 hours at 0° C., a yellowish precipitate separates out of this concentrated extract. This precipitate is filtered off with suction and washed with ice-cold acetic ester. The precipitate is discarded.

The filtrate is washed twice with 100 ml of water (ph 7.0) each time, and the water phases are back-extracted once with acetic ester, all the acetic ester phases are combined, dried with sodium sulphate, filtered and the solvent is completely removed under high vacuum at 0° C.

If the acetic ester extract was still pale yellow in color, then the crude extract has a brown color. In the case of fermentation of Tü 1922 in a 100 liter fermenter, about 4.7 g of crude extract are obtained in this manner.

4.7 g of this crude product are dissolved in 30 ml of chloroform/methanol 1:1 (parts by volume) and separated into 15 ml fractions on 400 g silica gel column (silica gel 60; particle size 0.063–0.200 mm; MERCK) using a mixture of chloroform and methanol 9:1 (parts by volume) as the eluant. Changeover to 100% methanol is made after fraction 60. Column: 200 cm×35 mm.

Based on TLC checks, the following fractions (Fr.) are combined and the solvent is removed by distillation:

| Fr. | 1–6 | 0.70 g | fats |
|---|---|---|---|
| Fr. | 7–11 | 2.60 g | $A_1/A_2$ and fats, a little $B_1/B_2$ |
| Fr. | 12–19 | 0.50 g | $B_1/B_2$ and a little $A_1/A_2$ |
| Fr. | 20–28 | 0.15 g | $B_1/B_2$ |
| Fr. | 29–43 | 0.40 g | no bafilomycin components |
| Fr. | 44–60 | 0.14 g | no bafilomycin components |
| Fr. | 61–91 | 0.27 g | undesired products |

Material from fractions 7–11 (2.6 g) is called crude $A_1/A_2$ and that from fractions 12 to 28 (0.65 g) is called crude $B_1/B_2$.

Fractions 44–91 are discarded.

Thin-layer chromatographic checks (TLC checks) are carried out on MERCK TLC ready-coated silica gel 60 F. 254 plates, layer thickness 0.25 mm, using the solvent system $CHCl_3/CH_3OH$ 9:1 (parts by volume).

The active components can be characterized by UV (254/366 nm), spraying with (a) concentrated $HCl/CH_3OH$ (30/70 parts by volume) (red coloration) and (b) iodine spray reagent (0.2 g of iodine + 0.4 KI in 50 ml of water and 50 ml of ethanol).

Major components: Rf value.
$B_1/B_2$: 0.38–0.43.
$A_1/A_2$: 0.54.

3. Final purification of the bafilomycins (a) Bafilomycins $A_1$ and $A_2$

Crude $A_1/A_2$ is dissolved in 20 ml of chloroform and again separated on a 300 g silica gel column (150 cm×3 cm, silica gel 60, 0.063–0.200 mm, WOELM) using chloroform/methanol 95:5 (parts by volume). Fractions 15–29 contain 0.68 g of prepurified $A_1/A_2$ and fractions 21–29 contain 0.06 g of $B_1/B_2$ components. The major amount is fats, which are not characterized in detail, in fractions 1–14 (1.4 g).

An additional 0.08 g of $A_1/A_2$ components result from the prepurification of $B_1/B_2$. According to HPLC investigations, the combined fractions 14–17 contain 65% of $A_1$, while the 0.08 g contains 85% $A_2$ (fraction volume: 15 ml).

The two prepurified compounds $A_1$ and $A_2$ are combined (0.76 g) and separated on a 150 g silica gel column (150 cm×2 cm, silica gel 60, 0.063–0.200 nm, WOELM) using ethyl methyl ketone/chloroform 1:1 (parts by volume) as the eluant. Fractions (10 ml) 1–6 contain, in 0.58 g, $A_1$ in addition to fats, and fractions 7–12 (0.15 g) contain $A_2$. For final removal of the fats, the combined fractions 1–6 are separated by preparative HPLC.

The procedure with fractions 7–12 is the same. The fractions of both preparative separations are combined and again separated on a preparative RP-18 column. 45 mg of $A_1$ (92% pure) and 36 mg of $A_2$ (95% pure) are eluted. The substances are obtained after removal of the solvent by distillation.

Some supplementary data on the HPLC separation (high pressure liquid chromatography), which can be carried out with commercial equipment and materials:

Pump: KNAUER type 52.00.
Injector: RHEODYN 7125 with a 2 ml sample loop.
Column: KNAUER 25 cm×16 mm in diameter.
Packing material: MERCK RP-18 10 μm (silica gel, modified with aliphat ($C_{18}$)).
Eluant: Methanol/water 80:20 (parts by volume) pH 7.0.
Flow rate: 10 ml/minute.
Detection: UV absorption at 290 nm.
Fraction volume: 15 ml.

35 mg of $A_1$ are contained in fractions 5–7, and 15 mg of a mixture of $A_2$ and impurities are contained in fractions 8–10. The fats which are retained on the column are eluted overnight with methanol and discarded.

(b) Compounds $B_1$ and $B_2$

The 0.65 g of $B_1/B_2$ (compare rough purification) is supplemented by 0.06 g of the same mixture from the final purification of $A_1/A_2$. These combined fractions (0.71 g) are separated on a 150 g silica gel column (silica gel 60, 0.063–0.200 mm, MERCK) using chloroform/methanol 9:1 (parts by volume) as the eluant (column dimension: 150 cm×2 cm, fraction volume: 10 ml). Fractions 16–28 contain 0.22 g of $B_1/B_2$, and 0.08 g of $A_1/A_2$ can be isolated from fractions 8–13.

The prepurified 0.22 g of $B_1/B_2$ components are separated on a 50 g silica gel column (100×1 cm, silica gel 60, 0.063–0.200 mm, WOELM), first with the eluant mixture chloroform/acetic ester 1:1 (parts by volume) and, after one column volume, with 100% acetic ester. Fraction volume: 10 ml. Fractions 18–25 contain 0.09 g of $B_1$ (94% pure) and fractions 26–38 contain 0.04 g of $B_2$ (67% pure), which are obtained after removal of the solvent by distillation.

Bafilomycin $B_1$ has been described above. Bafilomycin $B_2$ differed from Bafilomycin $B_1$ in the thin-layer chromatogram:

| Mobile phase | RF $B_1$ | RF $B_2$ |
|---|---|---|
| $CHCl_3$-$CH_3OH$ 9:1 (parts by volume) | 0.43 | 0.38 |
| EMK - $CHCl_3$ 1:1 (parts by volume) | 0.37 | 0.40 |
| EMK | 0.78 | 0.81 |
| Acetone | 0.76 | 0.82 |

EMK = ethyl methyl ketone

III. Example for the acylation of the bafilomycins 1 ml of acetic anhydride is added to a solution of 23 mg of $A_1$ (87% pure, containing 12% $A_2$) in 3 ml of pyridine, and the mixture is stirred in the dark at 20° C. for 24 hours. It is then poured onto 60 ml of ice and the mixture is extracted 3 times with 10 ml of chloroform each time. The organic phases are washed with water, dried with sodium sulphate and the solvent is removed in vacuo. The yellowish reaction product is immediately dissolved in 1 ml of methanol and separated on a HPLC column (25 cm × 16 mm internal diameter) on RP-18 10 μm MERCK using methanol/water 80:20 (parts by volume) pH 7.0, flow rate 10 ml/minute, detection; UV absorption at 290 nm.

The following compounds of the formula I are obtained in this manner, their structure being determined by spectroscopic methods (IR, NMR and mass spectra):

(a) R=H; $R^1$=H; $R^2$=—$COCH_3$ yield: 6 mg.
(b) R=$COCH_3$; $R^1$=H; $R^2$=—$COCH_3$ yield: 10 mg.
(c) R=$COCH_3$; $R^1$=$CH_3$; $R^2$=—$COCH_3$ yield: 2 mg.

The products will be further identified with reference to the accompanying drawings which are UV, IR and NMR spectra successively and respectively of $A_1$, $A_2$ and $B_1$ (FIGS. 7 and 8) or $B_2$ (FIG. 9).

Detailed Explanation of FIGS. 1 to 9

1. General explanations

1. UV spectra: FIG. 1: $A_1$; FIG. 4: $A_2$; FIG. 7: $B_1$;
Abscissa: Wavelength (nm);
Ordinate: Extinction (molar extinction coefficient $\epsilon$);
Solvent: Methanol.

2. IR spectra: (in KBr): FIG. 2: $A_1$; FIG. 5: $A_2$; FIG. 8: $B_1$;
Abscissa: Wavelength (μm) or wave number ($cm^{-1}$);
Ordinate: Transmittance (%).

3. NRM spectra:
$^1H$-NMR spectra, recorded at 400 MHz;
Internal standard: tetramethylsilane (TMS);
Chemical shift in ppm; Solvent and concentrations:
FIG. 3 ($A_1$): $CDCl_3$, c=10 mg/ml;
FIG. 6 ($A_2$): $CDCl_3$, c=12 mg/ml;
FIG. 9 ($B_2$): $CDCl_3$, c=10 mg/ml.

Explanation of some company names and trademarks which are mentioned

MERCK: denotes Messrs. E. Merck, Darmstadt, Federal Republic of Germany.

WOELM: denotes Messrs. Woelm, Eschwege, Federal Republic of Germany.

KNAUER: denotes Messrs. Knauer, Berlin, Federal Republic of Germany.

RHEODYN: is a trademark of Messrs. Knauer, Berlin, Federal Republic of Germany.

The biological efficacy of the compounds according to the invention will be illustrated by means of the examples which follow:

EXAMPLE A

Phaedon test

Solvent: 3 parts by weight of acetone.
Emulsifiers: 1 part by weight of alkylaryl polyglycol ether.

To produce a suitable preparation of active compound, 1 part by weight of the active compound is mixed with the stated amount of solvent and the stated amount of emulsifier, and the concentrate is diluted with water to the desired concentrations.

Cabbage plants (*Brassica oleracea*) are treated by being sprayed with the preparation of active compound of the desired concentration. After the spray coating has dried on, a leaf is removed from the treated plant and is placed in a plastic container and infested with larvae of the mustard beetle (*Phaedon cochleariae*). After 2 to 4 days, in each case one further leaf from the same plant is used as subsequent feed.

After the desired period of time, the destruction in % is determined. 100% means that all the animals have been killed; 0% means that none of the animals have been killed.

In this residue, bafilomycin $B_1$, for example, at a concentration of 0.004% shows a destruction of 100% after 14 days, and bafilomycin $A_1$, for example, at a concentration of 0.02% shows a destruction of 100% after 14 days.

EXAMPLE B

Plutella test

Solvent: 3 parts by weight of acetone.
Emulsifier: 1 part by weight of alkylaryl polyglycol ether.

To produce a suitable preparation of active compound, 1 part by weight of the active compound is mixed with the stated amount of solvent and the stated amount of emulsifier, and the concentrate is diluted with water to the desired concentrations.

Cabbage plants (*Brassica oleracea*) are treated by being sprayed with the preparation of active compound of the desired concentration. After the spray coating has dried on, a leaf is removed from the treated plant and is placed in a plastic container and infested with caterpillars of the diamond-back moth (*Plutella maculipennis*). After 2 to 4 days, in each case one further leaf from the same plant is used as subsequent feed.

After the desired period of time, the destruction in % is determined. 100% means that all the animals have been killed; 0% means that none of the animals have been killed.

In this test, bafilomycin $B_1$, for example, at a concentration of 0.004% shows a destruction of 100% after 14 days, and bafilomycin $A_1$, for example, at a concentration of 0.05% shows a destruction of 100% after 14 days.

EXAMPLE C

Development-inhibition test using Dysdercus intermedius (cotton stainer)

Solvent: 3 parts by weight of acetone.

Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water to the desired concentrations.

10 nymphs of the cotton stainer in each plastic container are provided with a few cotton seeds and a roll of absorbent cotton impregnated with the preparation of the active compound. After the desired period of time, the destruction in % is determined. 100% means that all the animals have been killed; 0% means that none of the animals have been killed.

In this test, bafilomycin $B_1$, for example, at a concentration of 0.004% shows a destruction of 100% after 14 days, and bafilomycin $A_1$, for example, at a concentration of 0.01% shows a destruction of 100% after 14 days.

EXAMPLE D

Development-inhibition test using *Ceratitis capitata* (Mediterranean fruit fly)

Solvent: 3 parts by weight of acetone.

Emulsifier: 1 part by weight of alkylaryl polyglycol ether.

To produce a suitable preparation of active compound, 1 part by weight of active compound is mixed with the stated amount of solvent and the stated amount of emulsifier, and the concentrate is diluted with water to the desired concentrations.

20 eggs of the Mediterranean fruit fly are placed in each small container on mashed artificial feed. The feed is treated with the active compound at the stated concentration. The total of killed eggs, larvae, pupae and imagos, related to the number of eggs employed, gives the destruction in %.

100% means that all animals were killed; 0% means that none of the animals were killed.

In this residue, bafilomycin $B_1$, for example, at a concentration of 0.00016% shows a destruction of 100% after 21 days, and bafilomycin $A_1$, for example, at a concentration of 0.0008% shows a destruction of 100% after 14 days.

EXAMPLE E

Test using *Psoroptes cuniculi*

Solvent:
35 parts by weight of ethylene glycol monomethyl ether
35 parts by weight of nonylphenol polyglycol ether To produce a suitable preparation of active compound, 3 parts by weight of active compound are mixed with 7 parts by weight of the solvent mixture indicated above, and the concentrate thus obtained is diluted with water to the desired concentration.

About 10–25 *Psoroptes cuniculi* are placed in 1 ml of the preparation of active compound to be tested, which has been pipetted into the tablet recesses in a blister pack. The level of destruction is determined after 24 hours.

In this test, bafilomycins $A_1$ and $B_1$, for example, at a concentration of 80 ppm showed a destruction of 100%.

EXAMPLE F

Test using *Lucilia cuprina* res. larvae

Emulsifiers:
35 parts by weight of ethylene glycol monomethyl ether
35 parts by weight of nonylphenol polyglycol ether To produce a suitable preparation of active compound, 3 parts by weight of active compound are mixed with 7 parts by weight of the solvent mixture indicated above, and the concentrate thus obtained is diluted with water to the desired concentration in each case.

About 20 *Lucilia cuprina* res. larvae are placed in a test tube which contains about 1 cm$^2$ of horse meat and 0.5 ml of the preparation of active compound. The level of destruction is determined after 24 hours.

In this test, bafilomycin $B_1$, for example, at a concentration of 80 ppm showed a destructive effect of about 95%.

EXAMPLE G

Tetranychus test (resistant)

Solvent: 3 parts by weight of acetone

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this residue, bafilomycin $A_1$, for example, at a concentration of 0.1% shows a destruction of 100% after 7 days, and bafilomycin $B_1$, for example, at a concentration of 0.02% shows a destruction of 100% after 7 days.

EXAMPLE H

*Cochliobolus sativus* test (barley)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compounds until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

Compared with the untreated control (100% infestation), treatment with bafilomycin $A_1$ showed an infestation of only 41.2%, and with bafilomycin $B_1$ an infestation of only 12.5% (concentrations of active compound: 0.025%).

EXAMPLE I

Pyrenophora teres test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Pyrenophora teres*. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

Compared with the untreated control (100% infestation), treatments with bafilomycin $A_1$ and bafilomycin $B_1$ showed an infestation of only 12.5% (concentrations of active compound 0.025%).

EXAMPLE K

Botrytis test (bean)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, two small pieces of agar coated with *Botrytis cinerea* are placed on each leaf. The inoculated plants are placed in a darkened, moist chamber at 20° C. 3 days after the inoculation, the size of the infected spots on the leaves is rated.

Compared with the untreated control (100% infestation), treatments with bafilomycin $B_1$ showed an infestation of only 4%, at a concentration of active compound of 250 ppm.

EXAMPLE L

Phytophthora test (tomato)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating had dried on, the plants are inoculated with an aqueous suspension of spores of *Phytophthora infestans*.

The plants are placed in an incubation cabinet at 100% relative atmospheric humidity and about 20° C.

Evaluation is carried out 3 days after the inoculation.

Compared with the untreated control (90% infestation), treatment, with a concentration of active compound of 250 ppm, with bafilomycin $B_1$ showed an infestation of only 9%.

EXAMPLE M

Pellicularia test (rice)

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for activity, young rice plants in the 3- to 4-leaf stage are sprayed until dripping wet. The plants remain in a greenhouse until they have dried off. The plants are then inoculated with *Pellucularia sasakii* and are placed at 25° C. and 100% relative atmospheric humidity.

The evaluation of the disease infestation is carried out 5 to 8 days after the inoculation.

Compared with the untreated control (100% infestation), treatment with bafilomycin $B_1$ showed an infestation of 0% (concentration of active compound 0.025%).

The bafilomycin $B_1$ according to the invention also showed good activity in tests using *Puccinia recondita* on grain, *Pyricularia oryzae* on rice, and *Venturia inaequalis* on the apple.

EXAMPLE N

In vitro antimycotic activity

Description of the experiment:

The in vitro tests were carried out in the serial dilution test using inocula of organisms of, on average, $5 \times 10^3$ to $10^4$ organisms per ml of substrate. The nutrient media used were (a) for dermatophytes and molds. Sabourand's milieu dépreuve (b) for yeasts: meat extract-glucose broth.

The incubation temperature was 28° to 37° C., and the incubation time was 24 to 96 hours for yeasts, and 96 hours for dermatophytes and moulds.

In this test, the compound $B_1$ according to the invention showed a good effect.

EXAMPLE O

In vitro nematodes test

The destruction and inhibition of multiplication of the nematode *Caenorhabditis elegans* are tested in a liquid medium in the presence of bacteria which serve to feed the nematodes.

In this test, bafilomycins $A_1$ and $B_1$ inhibited the multiplication of *C. elegans* by more than 90% at a concentration of 25 µg/ml.

EXAMPLE P

Puccinia Test (wheat)/protective/curative

Solvent: 100 parts by weight dimethylformamide
Emulsifier: 0.25 parts by weight alkylaryl polyglycol ether To produce a suitable preparation of active compound, 1 part by weight of active compound is mixed with the stated amounts of solvent and emulsifier, and the concentrate is diluted with water to the desired concentration.

To test with protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

Compared with the untreated control (100% infestation), treatment, with a concentration of active compound of 0.025%, with bafilomycin $A_1$ showed an infestation of 0%, and with bafilomycin $B_1$ an infestation of 12.5%.

As employed in the following claims, "pure" has reference to a product which is free of most of the naturally accompanying impurities with which it is associated in the culture medium. Advantageously, the combined desired materials are present in a concentration of more than about 85%, preferably more than about 95%, by weight of the solids recovered from selected fractions of the chromatographic separation. Such active "pure" material can be admixed with other active materials and/or diluents in conventional manner.

It will be appreciated that the instant specification and examples are set forth by way of illustration and not limitation, and that various modifications and changes may be made without departing from the spirit and scope of the present invention.

We claim:

1. Bafilomycin of the formula

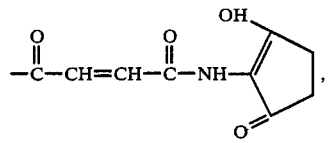

in which

R is hydrogen or the acyl radical of a carboxylic acid having one to six carbon atoms,
$R^1$ is hydrogen or $CH_3$, and
$R^2$ is hydrogen, the acyl radical of a carboxylic acid having one to six carbon atoms or the group

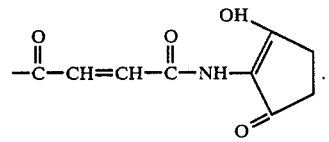

at least one of R and $R^2$ being the radical of a carboxylic acid acyl.

2. A Bafilomycin according to claim 1, in which the acyl radical is acetyl.

3. A pure Bafilomycin of the formula

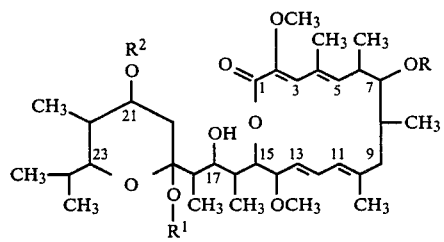

in which

R is hydrogen or the acyl radical of a carboxylic acid having one to six carbon atoms,
$R^1$ is hydrogen or $CH_3$, and
$R^2$ is hydrogen, the acyl radical of a carboxylic acid having one to six carbon atoms or the group

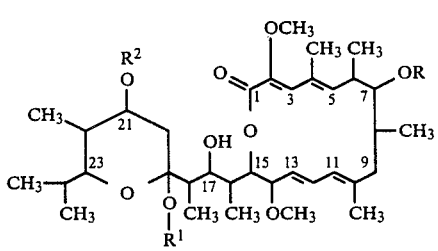

4. A Bafilomycin according to claim 3, in which the acyl radical is acetyl.

5. Bafilomycin $A_1$ according to claim 3 in which R, $R^1$ and $R^2$ are hydrogen and having the following properties:
Appearance: colorless amorphous powder,
Melting point: 98°–106° C. (decomposition),
Solubility:
  readily soluble in methanol,
  readily soluble in chloroform,
  sparingly soluble in water,
Thin-layer chromatogram (silica gel):
  $CHCl_3:CH_3OH$ (9:1 parts by volume),
  Rf: 0.51,
Ethyl methyl ketone: $CHCl_3$ (1:1 parts by volume)
  Rf: 0.42,
Ethyl methyl ketone:Rf: 0.86,
Acetone: Rf: 0.91,
Molecular weight: 622,
Molecular formula (elemental analysis): $C_{35}H_{58}O_9$,
Spectra:
  UV: FIG. 1,
  IR: FIG. 2,
  NMR: FIG. 3.

6. Bafilomycin $A_2$ according to claim 3 in which R and $R^2$ are hydrogen and $R^1$ is methyl, and having the following properties:
Appearance: colorless amorphous powder,
Melting point: 116°–119° C. (decomposition),
Solubility:

readily soluble in methanol,
readily soluble in chloroform,
sparingly soluble in water,
Thin-layer chromatogram:
  CHCl$_3$:CH$_3$OH (9:1 parts by volume),
  Rf: 0.52,
  Ethyl methyl ketone: CHCl$_3$ (1:1 parts by volume)
  Rf: 0.42,
  Acetone: Rf: 0.91,
Molecular formula (elemental analysis): C$_{36}$H$_{60}$O$_9$,
Spectra:
  UV: FIG. 4,
  IR: FIG. 5,
  NMR: FIG. 6,
Molecular weight: 636.

7. Bafilomycin B$_1$ according to claim 3 in which R and R$^1$ are hydrogen and R$^2$ is

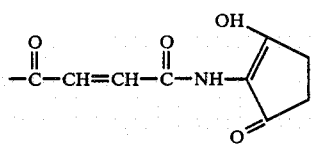

and having the following properties:
  Appearance: amorphous powder with an intense yellow color,
  Melting point: 89°–96° C. (decomposition),
  Solubility:
    readily soluble in methanol,
    readily soluble in chloroform,
    readily soluble in pyridine,
    soluble in ethyl acetate,
    sparingly soluble in water,
  Thin-layer chromatogram (silica gel):
    CHCl$_3$:CH$_3$OH (9:1 parts by volume),
    Rf: 0.43,
    Ethyl methyl ketone: CHCl$_3$ (1:1 parts by volume)
    Rf: 0.37,
    Ethyl methyl ketone: Rf: 0.78,
    Acetone: Rf: 0.76,
  Molecular weight: 815,
  Molecular formula (elemental analysis): C$_{44}$H$_{65}$O$_{13}$N,
  Spectra:
    UV: FIG. 7,
    IR: FIG. 8,
    NMR: FIG. 9.

8. Bafilomycin B$_2$ according to claim 3, in which R is hydrogen, R$^1$ is methyl and R$^2$ is

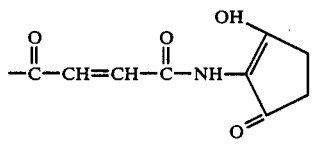

9. Bafilomycin according to claim 1, in which R and R$^1$ are hydrogen and R$^2$ is acetyl.

10. Bafilomycin according to claim 1, in which R and R$^2$ are acetyl and R$^1$ is hydrogen.

11. Bafilomycin according to claim 1, in which R is hydrogen, R$^1$ is methyl and R$^2$ is acetyl.

12. Bafilomycin according to claim 1, in which R and R$^2$ are acetyl and R$^1$ is methyl.

13. An insecticidal, arachnicidal, nematicidal or fungicidal composition comprising an insecticidally, arachnicidally, nematicidally or fungicidally effective amount of pure Bafilomycin according to claim 1 in admixture with a diluent.

14. An insecticidal, arachnicidal, nematicidal or fungicidal composition comprising an insecticidally, arachnicidally, nematicidally or fungicidally effective amount of pure Bafilomycin according to claim 3 in admixture with a diluent.

15. A method of combating insects, arachnids, nematodes or fungi which comprises administering thereto or to a habitat thereof an insecticidally, arachnicidally, nematicidally or fungicidally effective amount of Bafilomycin of the formula

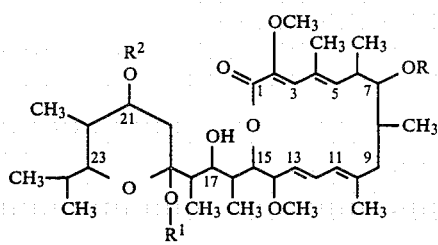

in which
R is hydrogen or the acyl radical of a carboxylic acid having one to six carbon atoms,
R$^1$ is hydrogen or CH$_3$, and
R$^2$ is hydrogen, the acyl radical of a carboxylic acid having one to six carbon atoms or the group

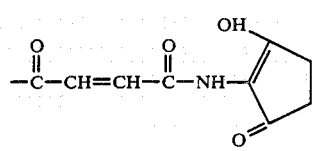

16. The method according to claim 15, wherein the Bafilomycin is selected from the group consisting of Bafilomycins wherein
(a) R, R$^1$ and R$^2$ are hydrogen,
(b) R and R$^2$ are hydrogen and R$^1$ is methyl,
(c) R and R$^1$ are hydrogen and R$^2$ is

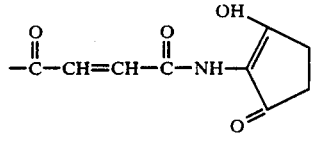

(d) R is hydrogen, R$^1$ is methyl and R$^2$ is

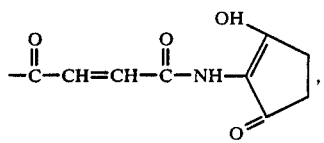

(e) R and R$^1$ are hydrogen and R$^2$ is acetyl,
(f) R and R$^2$ are acetyl and R$^1$ is hydrogen
(g) R is hydrogen, R$^1$ is methyl and R$^2$ is acetyl, and
(h) R and R$^2$ are acetyl and R$^1$ is methyl.

* * * * *